Jan. 28, 1941. N. J. HANSEN Plant Pat. 443
ROSE PLANT
Filed July 22, 1940
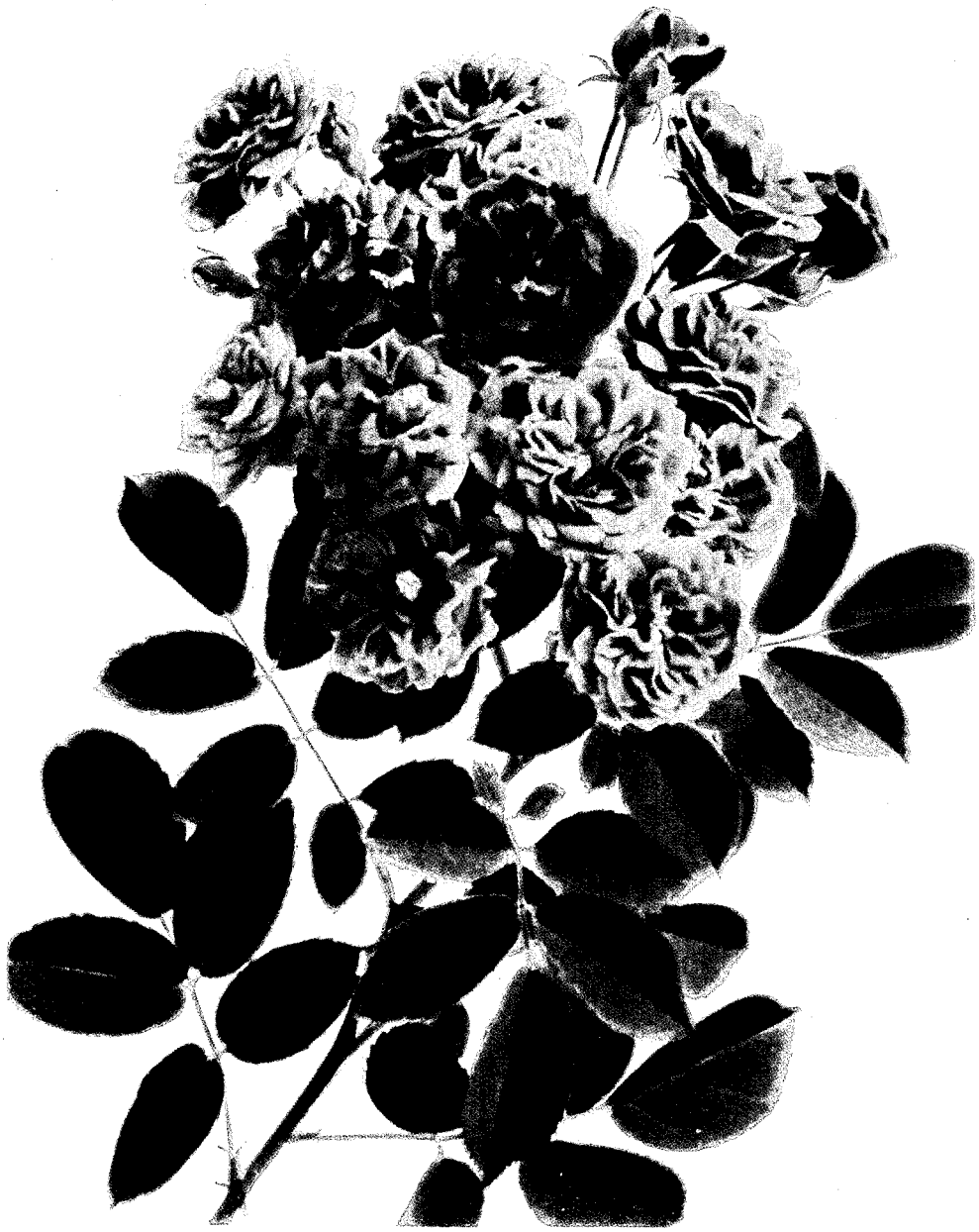
INVENTOR
Niels J. Hansen
By Orville M. Kile
Plant Patent Agt.

Patented Jan. 28, 1941

Plant Pat. 443

UNITED STATES PATENT OFFICE

443

ROSE PLANT

Niels J. Hansen, Washington, D. C., assignor to Bobbink & Atkins, East Rutherford, N. J.

Application July 22, 1940, Serial No. 346,856

1 Claim. (Cl. 47—61)

My present invention relates to a new and improved variety of rambler rose plant which is the result of definite breeding efforts made by me in the garden of Dr. Whitman Cross of Chevy Chase, Maryland. This new variety was produced by a cross of the varieties *Rosa soulieana* by Eblouissant, the resulting variety being very different from either of its parents.

My new variety has been asexually reproduced and its outstanding characteristics have proved to be permanently fixed.

The original illustration accompanying the application shows a cluster of the blossoms of my new variety, together with some of the foliage, in as nearly their true colors as the artist was able to show them. However, it was impossible to depict the velvety aspect of the newly opened flowers.

Following is a detailed description of the plant and flower of this new variety. Reference is made to the Maerz & Paul Dictionary of Color, except where the usual dictionary name is obviously intended.

*The plant*

Type or Class: Rambler.

Growth habit: Climbing; usually attains a height of about 15 feet. Branches freely from the canes rather than making all of its growth from the roots, more after the manner of a climbing rose than the usual rambler rose. Because of its type of growth it makes an excellent forcing rose.

Disease resistance: Very resistant to disease. Absolutely no mildew has ever been found on this variety.

Canes: Very strong and vigorous.

Stems: Stiff and upright, unlike the usual rambler. Color of the new wood falls in blocks 5 and 6—L of Plate 22. Old wood is darker.

Thorns: Large; downward-pointing; pink to bronze.

Foliage: Abundant. Leaves compound, usually five to seven leaflets.

*Leaflets.*—*Shape*—broadly oval, with obtuse apex. Inclined to fold at the midrib. *Edge*—regularly, sharply and shallowly serrated. *Size*—terminal leaflet averages 1½ inches by 1⅛ inches. Lateral leaflets progressively smaller toward stem. *Aspect*—glossy; smooth; veins prominent. *Substance* — leathery. *Color* — medium green, falling approximately in blocks 6 and 7—L of Plate 23.

Rachis: Light; deeply grooved on upper side; three or four small, sharp thorns occur on under side.

Stipules: Narrow; long; clinging except at points.

*The flower*

Inflorescence: Large cluster, composed of several umbel-like clusters growing from the leaf axes.

Bud:

*Shape.*—Globular.

*Size.*—Large for rambler roses.

*Peduncle and pedicels.*—Short; stiff.

*Color.*—Approximately in block 6—G of Plate 3.

*Opening.*—Very even.

*Sepals.*—Five; short; two or three usually finely branched or feathered.

Blossom:

*Borne.*—On strong stems in clusters of from 10 to 20 blossoms.

*Size.* — Individual blossoms average 1½ inches in diameter.

*Form.*—Full; imbricated.

*Petalage.*—Usually 60 to 70 petals.

*Color.*—Commonly referred to as "brilliant crimson." Neither Ridgway's Color Standards nor Maerz & Paul's Color Dictionary contains this color, but the nearest designation would be found on Plate 4, blocks 6—K and L, of the latter guide. The older flowers assume more of the tints found on Plate 3, blocks 6—G, H and I, and lose their velvety aspect with age.

*Fragrance.*—Slight.

*Longevity.*—Flowers last exceptionally well and fade very little.

Petals:

*Shape.*—Spatulate.

*Size.*—Outer petals average ¾ inch long by ½ inch wide.

*Aspect.*—Rich and velvety upon opening. Later lose their velvety sheen.

*Behavior.*—Cling until dead.

*Substance.*—Soft but firm.

Reproductive organs:

*Pistils.* — Many. *Styles* — white; *stigmas* — yellowish-white.

*Stamens.*—Few; surround bunched pistils. *Anthers*—light brown; *filaments*—same or slightly lighter.

*Ovary.*—Relatively large; globular.

*Seeds.*—This variety very seldom sets seeds.

*Comparison*

The variety known to me which my rose variety most resembles is the Crimson Rambler, but my new variety differs from the Crimson Rambler in many respects, principally as follows:

1. The growth and foliage of my new variety is more like that of a climber than of the usual rambler rose of which Crimson Rambler is an example.

2. The foliage of my new variety is immune to the usual rose diseases, no mildew or blackspot ever having been found on it. Crimson Rambler, on the other hand, is very susceptible to disease, particularly mildew.

3. The stems of my new variety are much stiffer and sturdier than those of Crimson Rambler, holding the clusters in an upright position.

4. The stems of my new variety branch freely from the cane instead of growing principally from the roots as is the habit of Crimson Rambler and most other ramblers.

5. The blooming season of my variety begins earlier and is of longer duration than that of Crimson Rambler.

6. My variety has the habit of sending out umbel-like axillary clusters of flowers, whereas Crimson Rambler and most other ramblers usually send out a single flower from each lateral axis.

7. The individual flowers in the clusters of my variety are much more double and more perfect in form.

8. Although both varieties fall in the red class, colors of the two varieties fall in entirely different ranges.

9. My new variety has a slight fragrance, which is lacking in most ramblers including Crimson Rambler.

10. The petals of the newly opened flowers of my variety have a velvety appearance which is lacking in the flowers of Crimson Rambler.

11. Not only is the blooming season of my variety longer than that of the Crimson Rambler, but the blossoms of my variety last much longer.

Having thus disclosed my invention, I claim:

A new and distinct variety of rose of the general rambler type, substantially as shown and described, characterized particularly by its sturdy growth, branching freely from the canes; its strong, stiff, long stems and stiff flower pedicels; its substantial, disease-resistant foliage; its early and long blooming season for ramblers; its large, closely packed clusters; and its long-lasting individual blossoms of unusually good form and large petalage for rambler roses, said blossoms having a slight fragrance, velvety appearance, and brilliant dark crimson color which fades only slightly.

NIELS J. HANSEN.